(12) United States Patent
Choi et al.

(10) Patent No.: US 10,201,447 B2
(45) Date of Patent: Feb. 12, 2019

(54) LINK ASSEMBLY AND MEMBER SUPPORTING APPARATUS USING THE SAME

(71) Applicant: Samsung Electronics Co., Ltd., Suwon-Si, Gyeonggi-Do (KR)

(72) Inventors: Hyun Do Choi, Yongin-si (KR); Yong jae Kim, Seoul (KR); Youn Baek Lee, Suwon-si (KR); Jeonghun Kim, Hwaseong-si (KR); Se-Gon Roh, Suwon-si (KR); Minhyung Lee, Anyang-si (KR); Jongwon Lee, Uiwang-si (KR); Byungjune Choi, Gunpo-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 260 days.

(21) Appl. No.: 14/478,099

(22) Filed: Sep. 5, 2014

(65) Prior Publication Data
US 2016/0038328 A1 Feb. 11, 2016

(30) Foreign Application Priority Data

Aug. 7, 2014 (KR) .......................... 10-2014-0101527

(51) Int. Cl.
*A61F 5/01* (2006.01)

(52) U.S. Cl.
CPC .......... *A61F 5/0125* (2013.01); *A61F 5/0102* (2013.01); *A61F 5/0123* (2013.01); *A61F 5/0127* (2013.01); *A61F 2005/0165* (2013.01); *A61F 2005/0169* (2013.01)

(58) Field of Classification Search
CPC .. A61F 5/00; A61F 5/01; A61F 5/0102; A61F 5/0123; A61F 5/0125; A61F 5/0127; A61F 2005/0165; A61F 2005/0169
USPC .................................. 601/5; 602/16, 23, 26
See application file for complete search history.

(56) References Cited

U.S. PATENT DOCUMENTS

| | | | |
|---|---|---|---|
| 2,591,373 A * | 4/1952 | Petruch ..................... | A61F 2/64 403/102 |
| 2007/0055189 A1 | 3/2007 | Katoh et al. | |
| 2008/0289670 A1 | 11/2008 | Ashihara et al. | |
| 2008/0318739 A1 | 12/2008 | Ashihara et al. | |

(Continued)

FOREIGN PATENT DOCUMENTS

| | | |
|---|---|---|
| CN | 101111211 A | 1/2008 |
| CN | 101188991 A | 5/2008 |

(Continued)

OTHER PUBLICATIONS

Chinese Office Action for corresponding Chinese Application No. 201510377206.0 dated Jun. 8, 2018.

(Continued)

*Primary Examiner* — Keri J Nelson
(74) *Attorney, Agent, or Firm* — Harness, Dickey & Pierce, P.L.C.

(57) ABSTRACT

Example embodiments relate to a link assembly and a leg supporting apparatus using the same. A top end of a frame mounted on a user's thigh can move along a downwardly-concave trajectory. A center of weight of the leg supporting apparatus placed on the top end of the frame converges on a lowest point of the downwardly-concave trajectory so that the user's weight can be stably supported.

28 Claims, 18 Drawing Sheets

(56) References Cited

U.S. PATENT DOCUMENTS

| | | |
|---|---|---|
| 2009/0199883 A1 | 8/2009 | Hiki |
| 2012/0259431 A1 | 10/2012 | Han et al. |
| 2013/0102934 A1 | 4/2013 | Ikeuchi |
| 2013/0226048 A1 | 8/2013 | Unluhisarcikli et al. |
| 2013/0296754 A1* | 11/2013 | Campbell ............ A61F 5/0123 602/16 |

FOREIGN PATENT DOCUMENTS

| | | |
|---|---|---|
| JP | 2010110465 A | 5/2010 |
| KR | 1020077028332 A | 2/2008 |
| KR | 1020070012082 B1 | 7/2008 |
| WO | WO-2012027336 A1 | 3/2012 |

OTHER PUBLICATIONS

European Office Action for corresponding European Application No. 15176195.4 dated Feb. 9, 2018.

* cited by examiner

… (1) …

LINK ASSEMBLY AND MEMBER SUPPORTING APPARATUS USING THE SAME

CROSS-REFERENCE TO RELATED APPLICATION

This application claims the benefit of priority from Korean Patent Application No. 2014-101527, filed on Aug. 7, 2014 in the Korean Intellectual Property Office, the disclosure of which is incorporated herein by reference in its entirety.

BACKGROUND

1. Field

Some example embodiments relate to a link assembly and/or a member supporting apparatus using the same that are capable of supporting a user's weight and assisting with walking.

2. Description of the Related Art

A member supporting apparatus such as, for example, a leg supporting apparatus, may be used as an assistance apparatus configured to assist a subject with weakened muscular strength and weight according to the field of usage or may also be used as a strengthening apparatus that increases a user's muscular strength and supports a load of a heavy object when transporting the heavy object.

SUMMARY

Some example embodiments provide a link assembly and/or a member supporting apparatus using the same that are capable of supporting a user's weight and assisting with walking.

Additional example embodiments will be set forth in part in the description which follows and, in part, will be obvious from the description, or may be learned by practice of the embodiments.

In accordance with at least one example embodiment, a leg supporting apparatus includes a calf frame mounted on a user's calf, and a thigh frame mounted on the user's thigh and pivotally connected to the calf frame and of which an end moves along a downwardly-concave curve when the thigh frame is pivoted with respect to the calf frame.

A point at which the thigh frame is pivoted in one direction regardless of a direction in which the calf frame is pivoted, may be included in a path on which the end of the thigh frame moves.

The point at which the thigh frame is pivoted in one direction regardless of the direction in which the calf frame is pivoted, may be a lowest point of the downwardly-concave curve.

The leg supporting apparatus may include a rotational force transferring member that transfers a rotational force to the thigh frame.

The rotational force transferring member may include at least one of a cable and a plurality of links.

A clutch may be mounted on a first joint to which the calf frame and the thigh frame are connected.

A rotational force using the rotational force transferring member may be selectively transferred to the thigh frame only when the clutch is in a locked state.

The leg supporting apparatus may further include a foot member pivotally connected to the calf frame.

A cam on which a first protrusion and a second protrusion are formed, may be disposed at a second joint to which the calf frame and the foot member are connected.

The first protrusion and the second protrusion formed on the cam may be asymmetrically formed.

A latch of which one side slides along an outer surface of the cam may be disposed on the calf frame.

A concave latch supporting portion may be disposed between the first protrusion and the second protrusion of the cam, and the latch may slide along the latch supporting portion.

The latch may include a roller sliding along the outer surface of the cam.

The leg supporting apparatus may further include a rotational force transferring member transferring a rotational force to the thigh frame, wherein one side of the rotational force transferring member may be fixed to the latch.

A guide groove guiding the rotational force transferring member may be formed in the latch.

In accordance with example embodiments, a link assembly includes a calf frame mounted on a user's calf and a thigh frame mounted on the user's thigh and connected to the calf frame so that the thigh frame operates in a walking mode, where the thigh frame is freely pivoted with respect to the calf frame or in a supporting mode, where the user's weight is supported together with the calf frame.

In the supporting mode, if an external force is applied, an end of the thigh frame may move along a downwardly-concave curve.

In the supporting mode, if the external force is removed, an end of the thigh frame may be placed at a lowest point of the downwardly-concave curve.

The link assembly may include a rotational force transferring member connecting the calf frame and the thigh frame and transferring rotation energy of the calf frame to the thigh frame.

A foot member may be mounted on the user's foot and may be connected to the calf frame.

A cam on which a protrusion is formed, may be mounted on the foot member.

A latch of which one side slides along an outer surface of the cam may be disposed on the calf frame.

A clutch may be disposed at a joint point to which the calf frame and the thigh frame are connected, and the clutch may be locked or unlocked by a switch.

A groove may be formed in the clutch, and a locking portion may be disposed on the switch so that the locking portion is inserted into the groove to lock the clutch.

When the clutch is locked, rotation energy of the calf frame may be transferred to the thigh frame using a rotational force transferring member that connects the calf frame and the thigh frame.

When the clutch is unlocked, the user may walk freely without an interference caused by a rotational force transferring member that connects the calf frame and the thigh frame.

In accordance with example embodiments, a leg supporting apparatus includes a first frame mounted on a user's thigh, a second frame pivotally connected to the first frame and mounted on the user's calf, a third frame pivotally connected to the second frame and mounted on the user's foot, a cam mounted on the third frame and on which a protrusion is formed, a latch mounted on the second frame and disposed to slide along an outer surface of the cam, and a rotational force transferring member connecting the latch and the first frame and transferring a rotational force to the first frame, wherein, when the first frame is pivoted with respect to the second frame, an end of the first frame may move along a downwardly-concave curve.

A clutch may be disposed at a joint portion to which the first frame and the second frame are connected, and when the clutch is in a locked state, a rotational force of the second frame may be transferred to the first frame through the rotational force transferring member.

When the clutch is unlocked, a rotational force of the second frame may not be transferred to the first frame.

According to at least one example embodiment, a supporting apparatus includes a first frame configured to be mounted on a first body portion, and a second frame configured to be mounted on a second body portion, the second frame being pivotally connected to the first frame, and an end of the second frame being configured to move along a given direction when the second frame is pivoted with respect to the first frame.

BRIEF DESCRIPTION OF THE DRAWINGS

These and/or other example embodiments will become apparent and more readily appreciated from the following description of the embodiments, taken in conjunction with the accompanying drawings of which.

DETAILED DESCRIPTION

Figure 1:
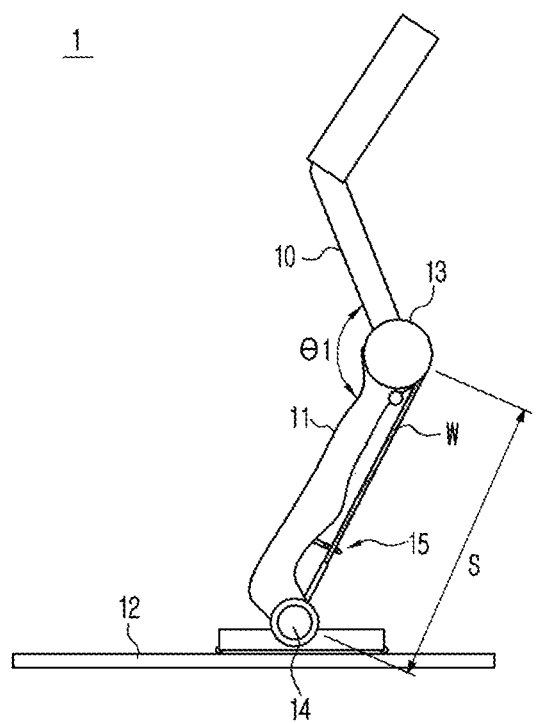
FIG. 1 is a conceptual view of a leg supporting apparatus according to an example embodiment.

Reference will now be made in detail to the example embodiments illustrated in the accompanying drawings, wherein like reference numerals refer to like elements throughout.

Hereinafter, a leg supporting apparatus according to an example embodiment will be described in detail with reference to the drawings.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

In the drawing figures, the dimensions of layers and regions may be exaggerated for clarity of illustration. Like reference numerals refer to like elements throughout. The same reference numbers indicate the same components throughout the specification.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

Figure 2A:
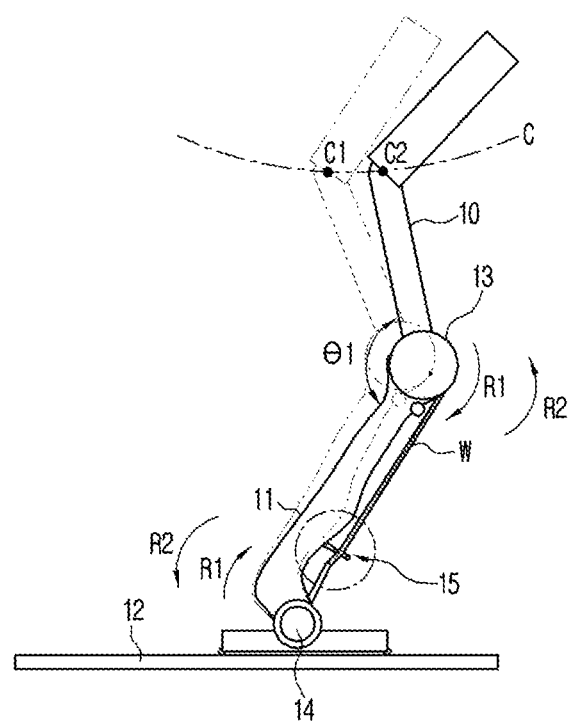
FIGS. 2A and 2B are views of the leg supporting apparatus in motion according to an example embodiment.
Figure 2B:
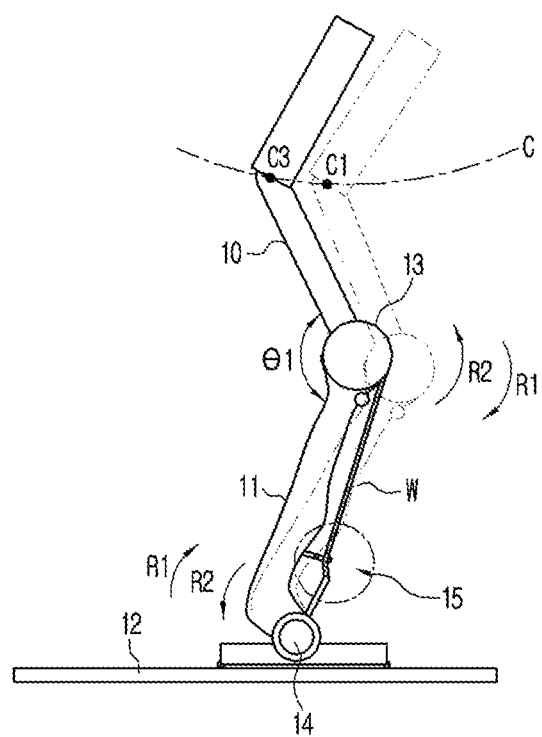

FIG. 1 is a conceptual view of a member supporting apparatus, such as, e.g., a leg supporting apparatus, according to an example embodiment, and FIGS. 2A and 2B are views of the leg supporting apparatus in motion, illustrated according to an example embodiment.

Referring to FIGS. 1 through 2B, a leg supporting apparatus 1 according to an example embodiment may support a user's weight without consuming energy from an energy source. The user may walk while wearing the leg supporting apparatus 1 and may use the leg supporting apparatus 1 as an apparatus for supporting his/her own weight as needed. In other words, the user may allot the entirety or part of the user's weight that is held by his/her own members such as, for example, a leg, to the leg supporting apparatus 1 as needed. For example, when a saddle that may support the user's hip is disposed on the leg supporting apparatus 1, the user may sit on the saddle and allot a force that is held by his/her own leg to the leg supporting apparatus 1, and then rest comfortably.

When the leg supporting apparatus 1 supports the user's weight, the leg supporting apparatus 1 may be provided in such a way that the center of weight of the leg supporting apparatus 1 to which the user's weight is added, may move along a downwardly-concave curve C. Thus, even though the leg supporting apparatus 1 makes a motion by an external force applied thereto, the center of weight of the leg supporting apparatus 1 is converged on a lowest point of the downwardly-concave curve C so that the user's weight can be stably supported.

Hereinafter, a structure of the leg supporting apparatus 1, of which the center of weight moves along the downwardly-concave curve C, will be described.

The leg supporting apparatus 1 includes a first frame 10 and a second frame 11 that may be configured to support the user's weight. The second frame 11 may be connected to the first frame 10 via a first joint 13 and may be connected to a third frame 12 via a second joint 14. The second frame 11 may be supported by the third frame 12.

The first frame 10 and the second frame 11 may be connected to each other via a cable W. One end of the cable W may be connected to the first joint 13, and the other end of the cable W may be connected to the second joint 14. For example, one end of the cable W may be fixed to the first joint 13 and may be connected to the first frame 10 that is pivotable with respect to the first joint 13, and the other end of the cable W may support the second joint 14 and may be connected to the non-moving third frame 12 or to a central axis of the second joint 14.

The cable W may be configured to move the first frame 10 as the second frame 11 is pivoted around the second joint 14. When the second frame 11 is pivoted around the second joint 14, a rotational force may be transferred to the first frame 10 via the cable W so that the first frame 10 may be pivoted around the first joint 13. In this case, an end of the first frame 10 may move along the downwardly-concave curve C.

Figure 3A:
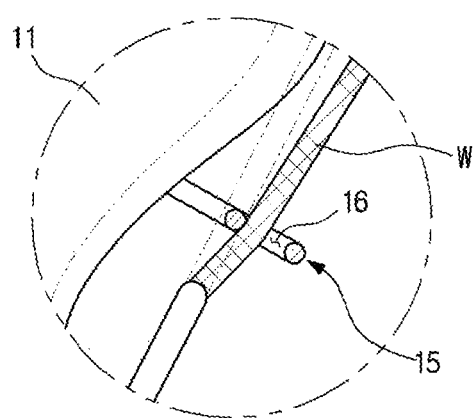
FIGS. 3A and 3B are views of a cable fixing portion of the leg supporting apparatus of FIG. 1, according to an example embodiment.

As illustrated in FIGS. 2A and 3A, when the second frame 11 is pivoted around the second joint 14 in one direction R1 in a state in which the end of the first frame 10 is placed at a lowest point C1 of the downwardly-concave curve C, the first frame 10 may be pulled by the cable W, and the first frame 10 may also be pivoted in the direction R1. When the first frame 10 is pulled by the cable W and is pivoted in the direction R1, an angle θ1 between the first frame 10 and the second frame 11 may be increased, and a top end of the first frame 10 may move upward along the downwardly-concave curve C and may be placed at a point C2 that is not the lowest point C1 of the downwardly-concave curve C.

In detail, when the second frame 11 is pivoted in the direction R1 in a state in which the top end of the first frame 10 is placed at the lowest point C1 of the downwardly-concave curve C, a minimum distance S between one side and the other side of the cable W may be decreased. When the minimum distance S between one side and the other side of the cable W is decreased, the first frame 10 fixed to one side of the cable W may be pulled in a downward direction. When the first frame 10 is pulled in the downward direction, the first frame 10 may be pivoted around the first joint 13 in the direction R1. When the first frame 10 is pivoted around the first joint 13, an angle θ1 formed by the first frame 10 and the second frame 11 may be increased. When the angle θ1 formed by the first frame 10 and the second frame 11 is increased, the top end of the first frame 10 may move upward along the downwardly-concave curve C.

When the second frame 11 is pivoted around the second joint 14 in another direction R2 in a state in which the top end of the first frame 10 is placed at the point C2, the minimum distance S between one side and the other side of the cable W may be increased, and the first frame 10 may be pivoted in the other direction R2. When the first frame 10 is pivoted in the other direction R2, the top end of the first frame 10 may move toward the lowest point C1 of the downwardly-concave curve C.

Figure 3B:
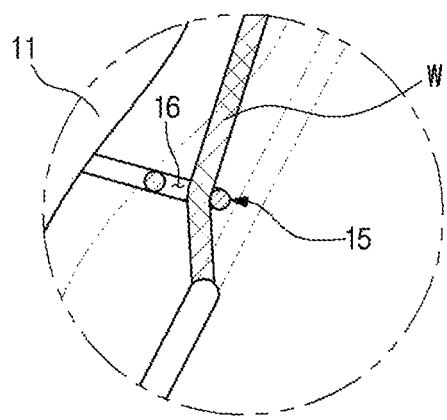

Even though the second frame 11 is pivoted in the other direction R2 in a state in which the end of the first frame 10 is placed at the lowest point C1 of the downwardly-concave curve C, the first frame 10 may pivot in the direction R1. As illustrated in FIGS. 2B and 3B, when the second frame 11 is pivoted around the second joint 14 in the other direction R2, the cable W may pull the first frame 10 so that the first frame 10 can pivot in the direction R1. In detail, when the second frame 11 pivots around the second joint 14 in the other direction R2, the minimum distance S between one side and the other side of the cable W may be decreased, and the first frame 10 may be pulled by the cable W. The first frame 10 pulled by the cable W may pivot in the direction R1 so that the angle θ1 between the first frame 10 and the second frame 11 can be increased. The top end of the first frame 10 may move upward along the downwardly-concave curve C and may be placed at a point C3 that is not the lowest point C1 of the downwardly-concave curve C.

When the second frame 11 is pivoted around the second joint 14 in the direction R1 in a state in which the top end of the first frame 10 is placed at the point C3, the minimum distance S between one side and the other side of the cable W may be increased, and the first frame 10 may pivot around the first joint 13 in the other direction R2. The top end of the first frame 190 may move to the lowest point C1 of the downwardly-concave curve C again.

In this way, when the second frame 11 is pivoted in the direction R1 or in the other direction R2, the top end of the first frame 10 may be predicted to move along the downwardly-concave curve C. When the center of weight of the leg supporting apparatus 1 is placed on the top end of the first frame 10, the center of weight of the leg supporting apparatus 1 may move along the downwardly-concave curve C. Even when the first frame 10 is pivoted around the first joint 13 by the external force applied to the first frame 10 and the top end of the first frame 10 is placed at the point C2 or C3 that is not the lowest point C1, if the external force is removed from the first frame 10, the first frame 10 may pivot around the first joint 13 in an opposite direction, and the top end of the first frame 10 may move to C1 that is the lowest point of the downwardly-concave curve C.

When an operation of the first frame 10 is considered in terms of energy, energy that is absorbed/discharged into/from the second frame 11 when the second frame 11 is rotated around the second joint 14, can be discharged/absorbed from/into the first joint 13. The first frame 10 is rotated in a direction in which the user's knee stretches/is bent, by the energy discharged/absorbed from/into the first joint 13. Thus, the top end of the first frame 10 and the center of weight of the leg supporting apparatus 1 may move along the downwardly-concave curve C. Accordingly, the user's center of mass in the leg supporting apparatus 1 may be converged on the lowest point C1 so that the user's weight can be stably supported.

A trajectory of the top end of the first frame 10 is not limited to the above description. For example, the top end of the first frame 10 may be moved along a straight line parallel to a bottom surface. Even when the top end of the first frame 10 moves along the straight line parallel to the bottom surface and an external force is applied to the leg supporting apparatus 1 and the first frame 10 or the second frame 11 is pivoted, a distance from the top end of the first frame 10 to a bottom end of the second frame 11 is not decreased so that the user's weight can be stably supported by the leg supporting apparatus 1.

Hereinafter, an example embodiment in which the top end of the first frame 10 moves along the downwardly-concave curve C, will now be described.

FIGS. 3A and 3B are views of a cable fixing portion according to an example embodiment.

Referring to FIGS. 3A and 3B, a cable fixing portion 15 may be disposed on the second frame 11. The cable fixing portion 15 may protrude from the second frame 11 to be approximately, or alternatively substantially, perpendicular to sides of the second frame 11. A cable through hole 16 through which the cable W passes, may be formed in the cable fixing portion 15. One side of the cable W may be fixed to the first joint 13 and connected to the first frame 10, and the other side of the cable W may be fixed to the third frame 12 or the central axis of the second joint 14. The cable W may extend in the form of a straight line from the first joint 13 to the third frame 12 or the central axis of the second joint 14.

When the second frame 11 is pivoted around the second joint 14, the cable W may be bent by an inner surface of the cable through hole 16. For example, as illustrated in FIG. 2A, when the second joint 14 is rotated in the direction R1 and the second frame 11 is pivoted in the direction R1 in a state in which the top end of the first frame 10 is placed at C1, the cable fixing portion 15 through which the cable W passes moves together with the second frame 11. Since the other side of the cable W is fixed to the third frame 12 or the central axis of the second joint 14, the cable W may extend in the form of a substantially straight line from the third frame 12 to the cable fixing portion 15 and may be bent at the cable fixing portion 15 and may extend in the form of a substantially straight line from the cable fixing portion 15 to the first joint 13. Since the cable W is bent at the cable fixing portion 15 and extends therefrom, the minimum distance S from one side to the other side of the cable W may be decreased, and the first frame 10 fixed to one side of the cable W may also be pulled downward so as to be rotated in the direction R1.

Similarly, as illustrated in FIG. 2B, even when the first joint 13 is rotated in direction R1 in a state in which the top end of the first frame 10 is placed at the lowest point C1 and the second joint 14 connected to the first joint 13 is rotated in the other direction R2 and the second frame 11 is pivoted in the direction R1, the cable W may move together with the second frame 11 in the direction R1. Since the cable W is bent at the cable fixing portion 15 and extends in the form of a straight line from the cable fixing portion 15 to the first joint 13, the minimum distance S from one side to the other side of the cable W may be decreased, the first joint 13 fixed to one side of the cable W may be rotated in the direction R1, and the first frame 10 connected to the first joint 13 may be pulled downward so as to be rotated in the direction R1.

Figure 4A:
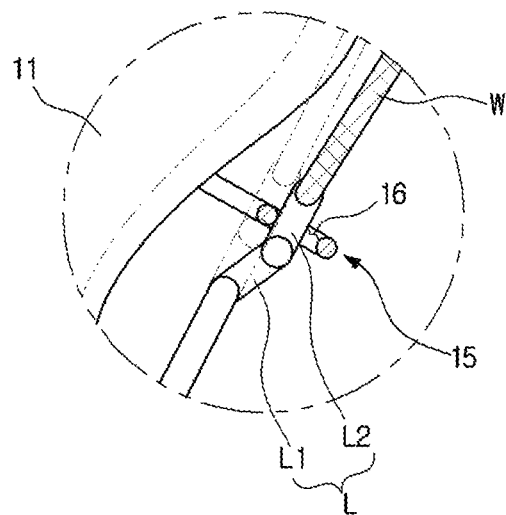
FIGS. 4A and 4B are views of a cable fixing portion of the leg supporting apparatus of FIG. 1, according to another example embodiment.
Figure 4B:
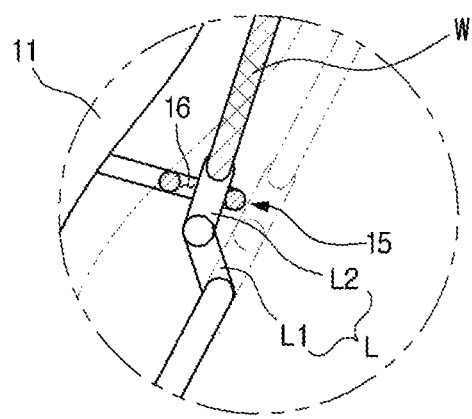

FIGS. 4A and 4B are views of the cable fixing portion 15 according to another example embodiment.

As illustrated in FIGS. 4A and 4B, a link L connected to the cable W may be placed in the cable through hole 16 of the cable fixing portion 15. The link L may include a first link L1 that is pivotally connected to the third frame 12 and a second link L2 that connects the first link L1 and the other side of the cable W. The second link L2 and the first link L1 may be pivotally connected to each other.

As illustrated in FIGS. 2A and 2B, when the second frame 11 is pivoted around the second joint 14 in the direction R1 or in the direction R2 in a state in which the top end of the first frame 10 is placed at the lowest point C1, the cable fixing portion 15 may move in a direction in which the second frame 11 is pivoted. When the cable fixing portion 15 moves and the inner surface of the cable through hole 16 pressurizes the link L, the second link L2 may be pivoted with respect to the first link L1 and may be bent at a connection portion of the second link L2 and the first link L1. Thus, a shortest distance between one side of the cable W fixed to the first joint 13 and the third frame 12 or the central axis of the second joint 14 is decreased after the second frame 11 is pivoted, so that the cable W may pivot the first joint 13 and the first joint 13 may be pulled downward so as to pivot the first frame 10 connected to the first joint 13.

Figure 5:
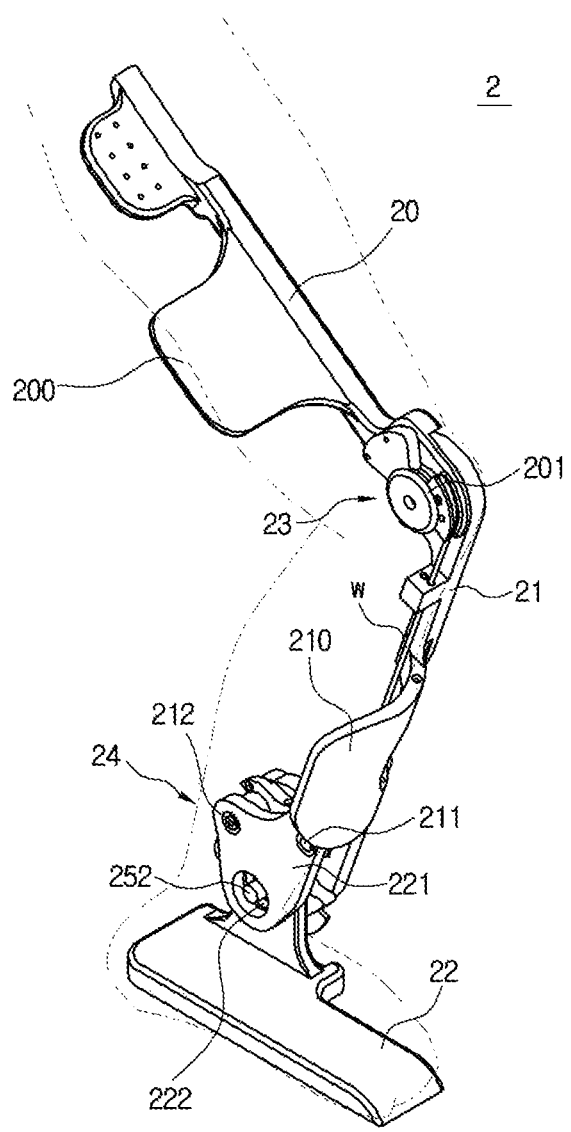
FIG. 5 is a view of a leg supporting apparatus according to an example embodiment.
Figure 6:
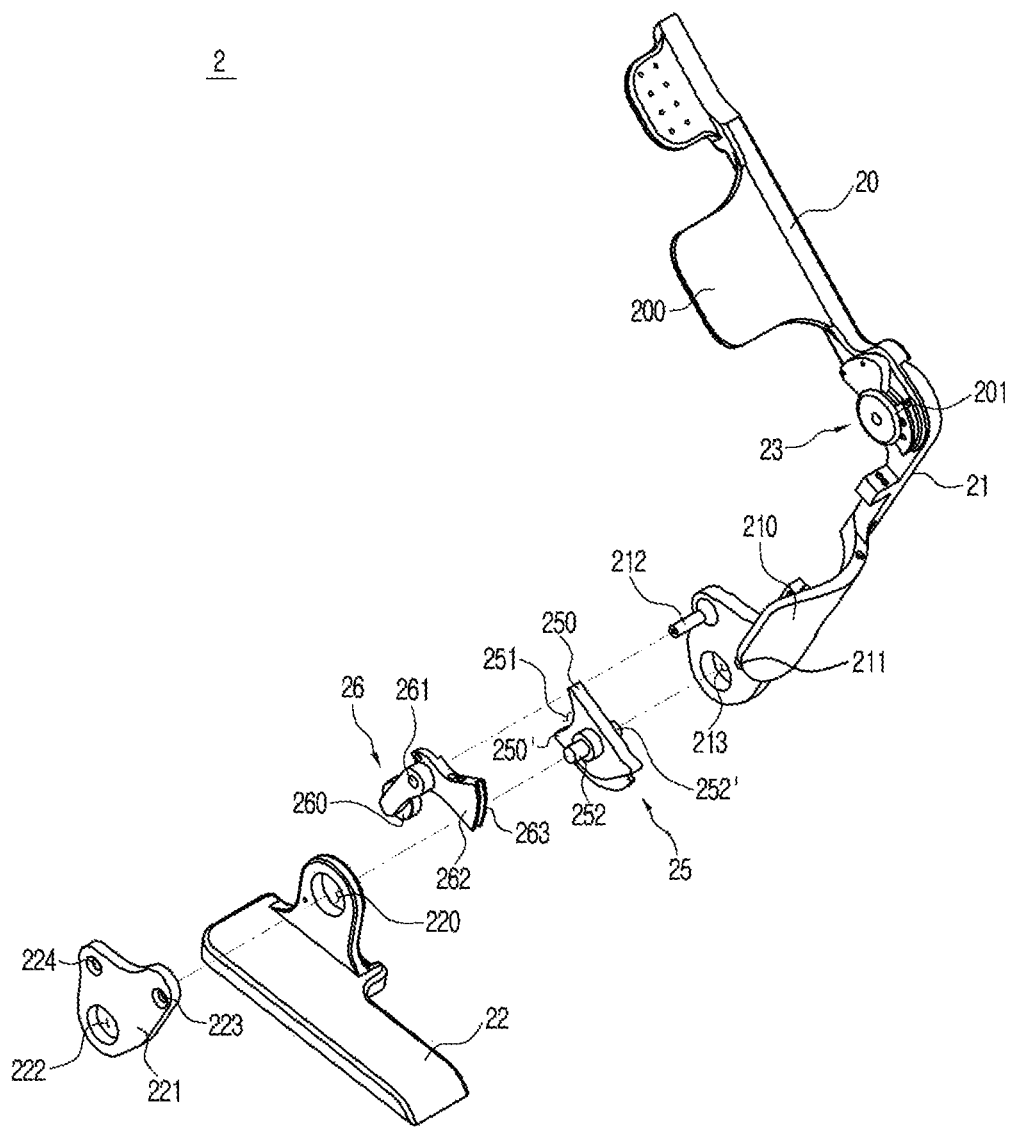
FIG. 6 is an exploded perspective view of the leg supporting apparatus according to an example embodiment.

FIG. 5 is an illustration of a leg supporting apparatus according to an example embodiment, and FIG. 6 is an exploded perspective view of the leg supporting apparatus according to an example embodiment.

Referring to FIGS. 5 and 6, a leg supporting apparatus 2 includes a first frame 20 and a second frame 21 pivotally connected to the first frame 20 through a first joint 23. The second frame 21 may be pivotally connected to the third frame 22 through a second joint 24. The second frame 21 may be supported by the third frame 22.

The first frame 20 may be mounted a member of the user's body. In the following example, the first frame 20 is mounted on the user's thigh. A first supporting portion 200 that may support the user's thigh may be disposed on the first frame 20. When the user wears the leg supporting apparatus 2, the first supporting portion 200 may be disposed at a rear portion of the user's thigh. The user may transfer his/her own weight to the leg supporting apparatus 2 through the first supporting portion 200 disposed at the rear portion of the user's thigh. In this way, the user's weight may be supported by the first supporting portion 200 that contacts the user's thigh. Also, a saddle (not shown) that may support the user's hip may be further disposed on the first frame 20.

The second frame 21 may be mounted on the user's calf. A second supporting portion 210 that may support the user's calf may be disposed on the second frame 21. When the user wears the leg supporting apparatus 2, the second supporting portion 210 may be disposed at a front portion of the user's calf. The user may transfer the user's weight to the leg supporting apparatus 2 through the second supporting portion 210 disposed at the front portion of the user's calf. In this way, the user's weight may be supported by the second supporting portion 210 that contacts the user's calf.

The user's weight may be supported by the leg supporting apparatus 2 in a state in which the user relaxes his/her own leg. The user's weight may be applied to the leg supporting apparatus 2 through the first supporting portion 200 that supports the user's thigh and the second supporting portion 210 that supports the user's calf.

A clutch 201 may be disposed at the first joint 23. In a walking mode in which the user walks while wearing the leg supporting apparatus 2, the clutch 201 causes the first frame 20 and the second frame 21 to be freely pivoted around the first joint 23. Thus, the user may walk while wearing the leg supporting apparatus 2. In this case, the clutch 201 may be in an unlocked state.

Figure 8A:
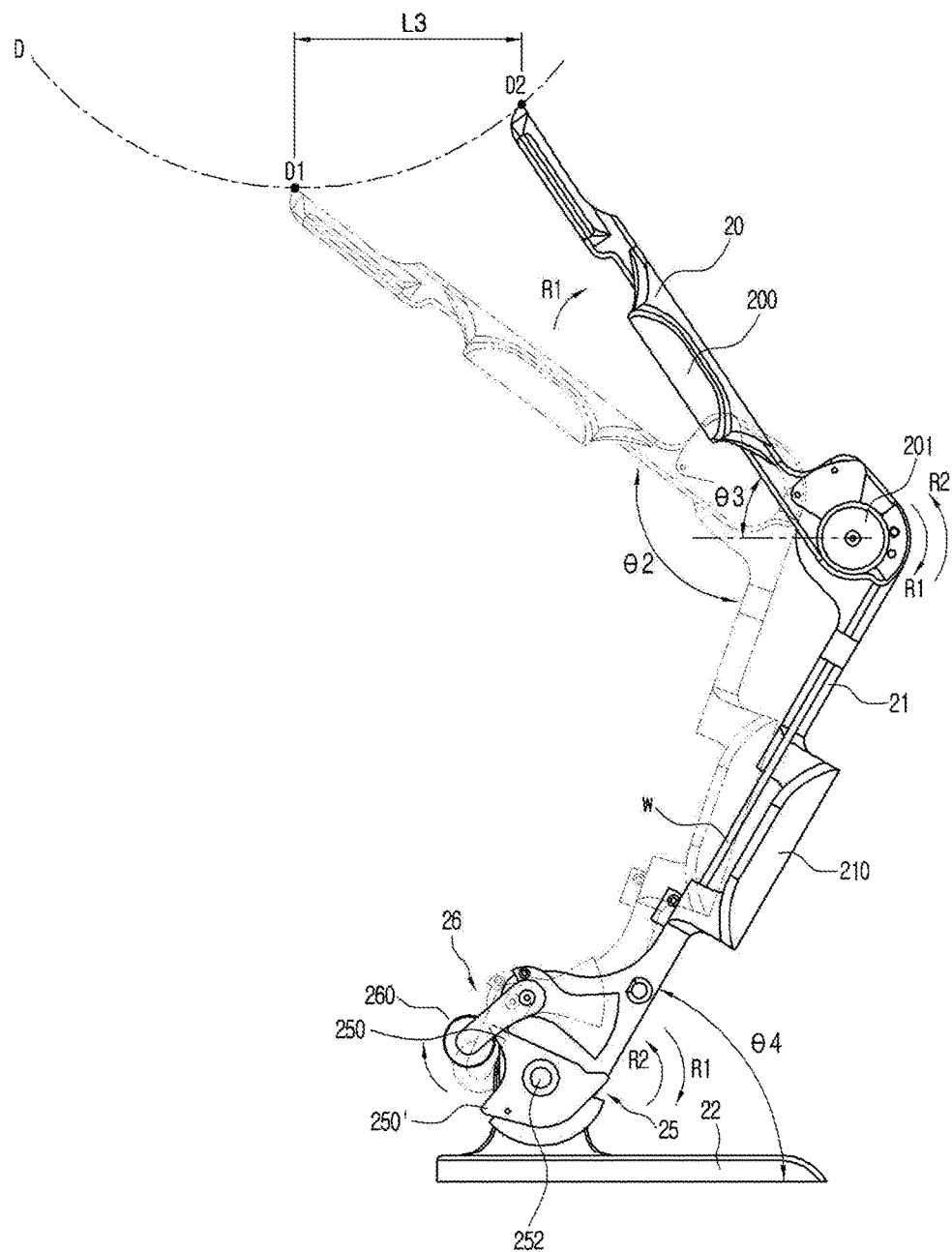
FIGS. 8A and 8B are views of the leg supporting apparatus in operation according to an example embodiment.

The user may set the clutch 201 to be in a locked state so that the user's weight can be supported by the leg supporting apparatus 2 in a state in which the user wears the leg supporting apparatus 2. When the clutch 201 is in the locked state and operates in a supporting mode in which the user's weight is supported, the first frame 20 may not be freely pivoted with respect to the second frame 21 but may be fixed to the second frame 21 so as to be pivoted with respect to the second frame 21 within a desired, or alternatively predetermined, angle (about ±30°). For example, as illustrated in FIG. 8A, when a top end of the first frame 20 is placed at a lowest point D1 of a downwardly-concave curve D, the first frame 20 may be fixed to the second frame 21 so that an angle formed by the first frame 20 and the second frame 21 may be θ2.

The angle θ2 formed by the first frame 20 and the second frame 21 when the top end of the first frame 20 is placed at the lowest point D1 of the downwardly-concave curve D may be set in consideration of an angle formed by the user's thigh and the user's calf at which the user is comfortable when the user's weight is supported by the leg supporting apparatus 2. For example, the angle θ2 formed by the first frame 20 and the second frame 21 may be an angle between about 60° and 135°, and in particular, at an angle between about 90° and 135°. As described above, the first frame 20 and the second frame 21 may be pivoted with respect to each other within about ±30° based on the angle set when the top end of the first frame 20 is placed at the lowest point D1 of the downwardly-concave curve D.

The second frame 21 may be connected to the third frame 22 so as to be pivoted around the second joint 24. A cam 25 may be disposed on the third frame 22. A hole 213 may be formed in the second joint 24 of the second frame 21. A hole 220 may be formed in the third frame 22. Shafts 252 and 252' may be disposed on both sides of the cam 25 facing each other. The shafts 252 and 252' may be configured to pass through the hole 220 formed in the third frame 22 and the hole 213 formed in the second frame 21, respectively.

One shaft 252 may pass through the hole 220 on one side of the third frame 22, and a coupling member may be coupled to an end of the shaft 252. Thus, the cam 25 may be fixed to the third frame 22. The other shaft 252' may pass through the hole 213 of the second frame 21, and an interference member may be coupled to an end of the shaft 252' so that the shaft 252' may not escape from the hole 213. The second frame 21 may be disposed to be rotated around the shaft 252'.

A mounting bracket 221 may be further disposed on the other side of the third frame 22. A first fixing hole 222, a second fixing hole 223, and a third fixing hole 224 may be formed in the mounting bracket 221. The shaft 252 disposed on the cam 25 may be inserted into the first fixing hole 222. The coupling member may be coupled to the shaft 252 outside of the mounting bracket 221. The mounting bracket 221 is disposed to be rotated around the shaft 252.

A first shaft 211 and a second shaft 212 may be disposed on the second frame 21. The first shaft 211 disposed on the second frame 21 is inserted into the second fixing hole 223. The second shaft 212 disposed on the second frame 21 may be inserted into the third fixing hole 224. A latch 26 may be disposed between the second frame 21 and the mounting bracket 221. The second shaft 212 may pass through a central hole 261 formed in the latch 26. The latch 26 may be disposed to be rotated around the second shaft 212 that passes through the central hole 261.

Figure 7:
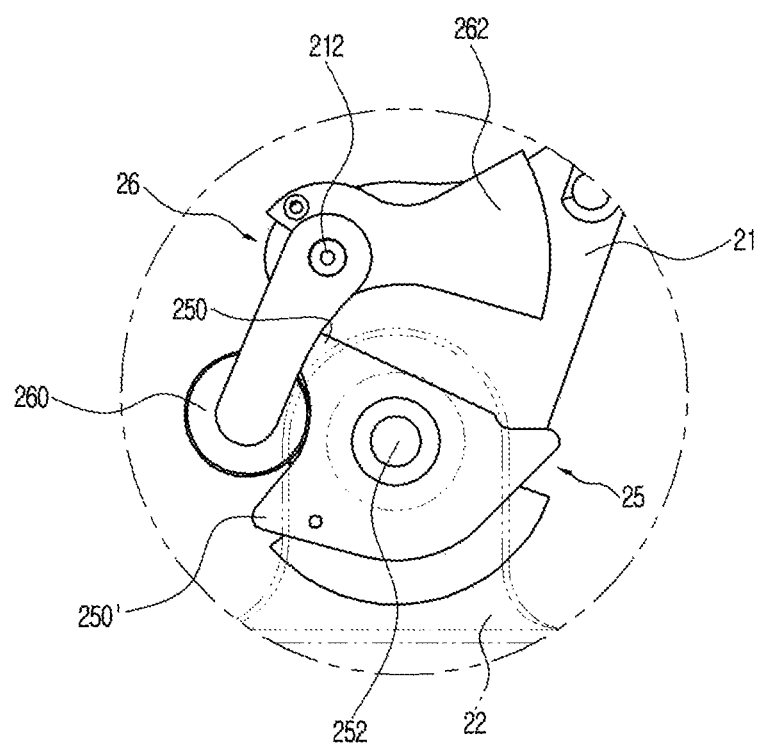
FIG. 7 is a view of an ankle joint portion of the leg supporting apparatus according to an example embodiment.

FIG. 7 is a view of an ankle joint portion of the leg supporting apparatus 2 according to an example embodiment.

Referring to FIGS. 6 and 7, a first protrusion 250 and a second protrusion 250' may be formed on one side of the cam 25. The first protrusion 250 and the second protrusion 250' may be symmetrically or asymmetrically formed. A concave latch supporting portion 251 may be formed between the first protrusion 250 and the second protrusion 250'.

When the user's weight is supported by the leg supporting apparatus 2, a roller 260 may be supported by the latch supporting portion 251 disposed on the cam 25. When the second frame 21 is pivoted, the latch 26 may rotate around the second shaft 212 disposed at a lower side of the second frame 21, and the roller 260 that is rotatable and is disposed at one side of the latch 26 may slide along the latch supporting portion 251 of the cam 25. For example, when the second frame 21 is rotated in the direction R1, the roller 260 may slide along the latch supporting portion 251 toward the first protrusion 250, and when the second frame 21 is rotated in the other direction R2, the roller 260 may slide along the latch supporting portion 251 toward the second protrusion 250'.

The latch 26 and the first frame 20 may be connected to each other using a cable W. One end of the cable W may be fixed to the latch 26, and the other end of the cable W may be fixed to the first joint 23. An additional bracket 262 may be mounted on the latch 26, and one end of the cable W may be fixed to the bracket 262. A guide groove 263 may be formed in the bracket 262 so as to guide the cable W. One end of the cable W may be fixed to the bracket 262, and the cable W may be guided by the guide groove 263 so that the other end of the cable W may be fixed to the first joint 23.

Figure 8B:
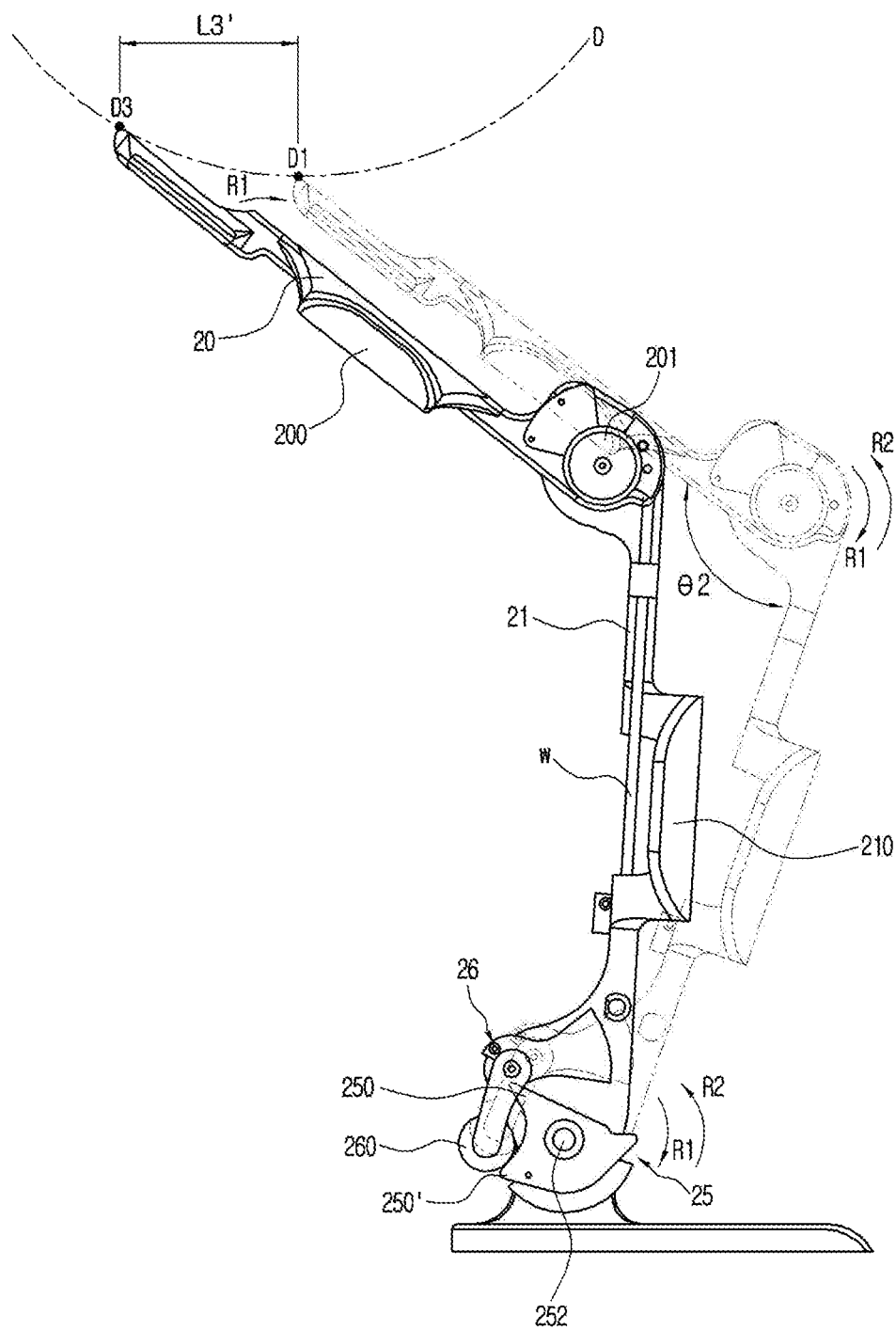

FIGS. 8A and 8B are views of the leg supporting apparatus in operation according to an example embodiment.

Referring to FIG. 8A, when the second frame 21 is pivoted around the second joint 24 in the direction R1 by an external force applied to the second frame 21 in a state in which the user's weight is supported by the leg supporting apparatus 2, and a top end of the first frame 20 is placed at the lowest point D1 and the roller 260 of the latch 26 slides along the latch supporting portion 251 of the cam 25 toward the first protrusion 250, the cable W may pull the first frame 20. When the first frame 20 is pulled by the cable W, the first frame 20 may be rotated around the first joint 23 in the direction R1 so that an angle between the first frame 20 and the second frame 21 may be greater than θ2. As the angle between the first frame 20 and the second frame 21 is greater than θ2, the top end of the first frame 20 may be elevated. Since the second frame 21 is pivoted around the second joint 24 and the first frame 20 is pivoted around the first joint 23 and the top end of the first frame 20 is elevated upward, the top end of the first frame 20 may be elevated toward a point D2 by drawing the downwardly-concave curve D.

Referring to FIG. 8B, even though the second frame 21 is configured to pivot around the second joint 24 in the other direction R2 in a state in which the top end of the first frame 20 is placed at the lowest point D1, the first frame 20 may pivot around the first joint 23 in the direction R1. When the second frame 21 pivots around the second joint 24 in the other direction R2, the roller 260 of the latch 26 may slide along the latch supporting portion 251 of the cam 25 toward the second protrusion 250'. When the roller 260 slides along an outer surface of the second protrusion 250', the cable W may pull the first frame 20. When the first frame 20 is pulled by the cable W, the first frame 20 may be rotated around the first joint 23 in the direction R1. Thus, the angle between the first frame 20 and the second frame 21 is greater than θ2, and the top end of the first frame 20 may be elevated. The top end of the first frame 20 may move to a point D3 by drawing the downwardly-concave curve D.

In this way, when the first frame 20 is rotated around the second joint 24 in the direction R1 in a state in which the end of the first frame 20 is placed at the lowest point D1, the end of the first frame 20 may move to a right upward point D2, and when the second frame 21 is rotated around the second joint 24 in the other direction, the end of the first frame 20 may move to a left upward point D3. An upper range or a maximum distance (L3+L5') at which the end of the first frame 20 may move to the right and left, may vary according to the size of the third frame 22 and the size of the latch supporting portion 251. For example, an upper range for the distance (L3+L5'), for example a maximum range, at which the end of the first frame 20 may move to the right and left, may be about 5 to 60 cm, and in particular, about 20 to 40 cm.

An angle θ3 formed by the first frame 20 and a bottom surface that is a reference surface may be about −20° to 90°. That is, θ3 that is the angle formed by the first frame 20 and the bottom surface may be about 20° in a downward direction and about 90° in an upward direction. An angle θ4 formed by the second frame 21 and the bottom surface may be about 30° to 90°. In this case, the angle θ2 formed by the first frame 20 and the second frame 21 may be about 30° to 180°. Meanwhile, the leg supporting apparatus 1 may be configured in such a way that, in an initial configuration in which the end of the first frame 20 is placed at the lowest point D1, the angle θ3 formed by the first frame 20 and the bottom surface may be about 20° to 60° and the angle θ4 formed by the second frame 21 and the bottom surface may be about 40° to 75°. In the initial configuration, the angle θ2 formed by the first frame 20 and the second frame 21 may be about 60° to 135°.

Even when the user's weight is supported by the leg supporting apparatus 2 and the second frame 21 is pivoted around the second joint 24 by the external force applied to the second frame 21, if the top end of the first frame 20 is provided to move along the downwardly-concave curve D, the center of weight of the leg supporting apparatus 2 to which the user's weight is applied, may move along the downwardly-concave curve D. The center of weight of the leg supporting apparatus 2 to which the user's weight is applied, moves along the downwardly-concave curve D so that, even when an external force is applied to the leg supporting apparatus 2, the center of weight of the leg supporting apparatus 2 can be returned to the lowest point D1 and thus the user's weight can be stably supported.

Figure 9:
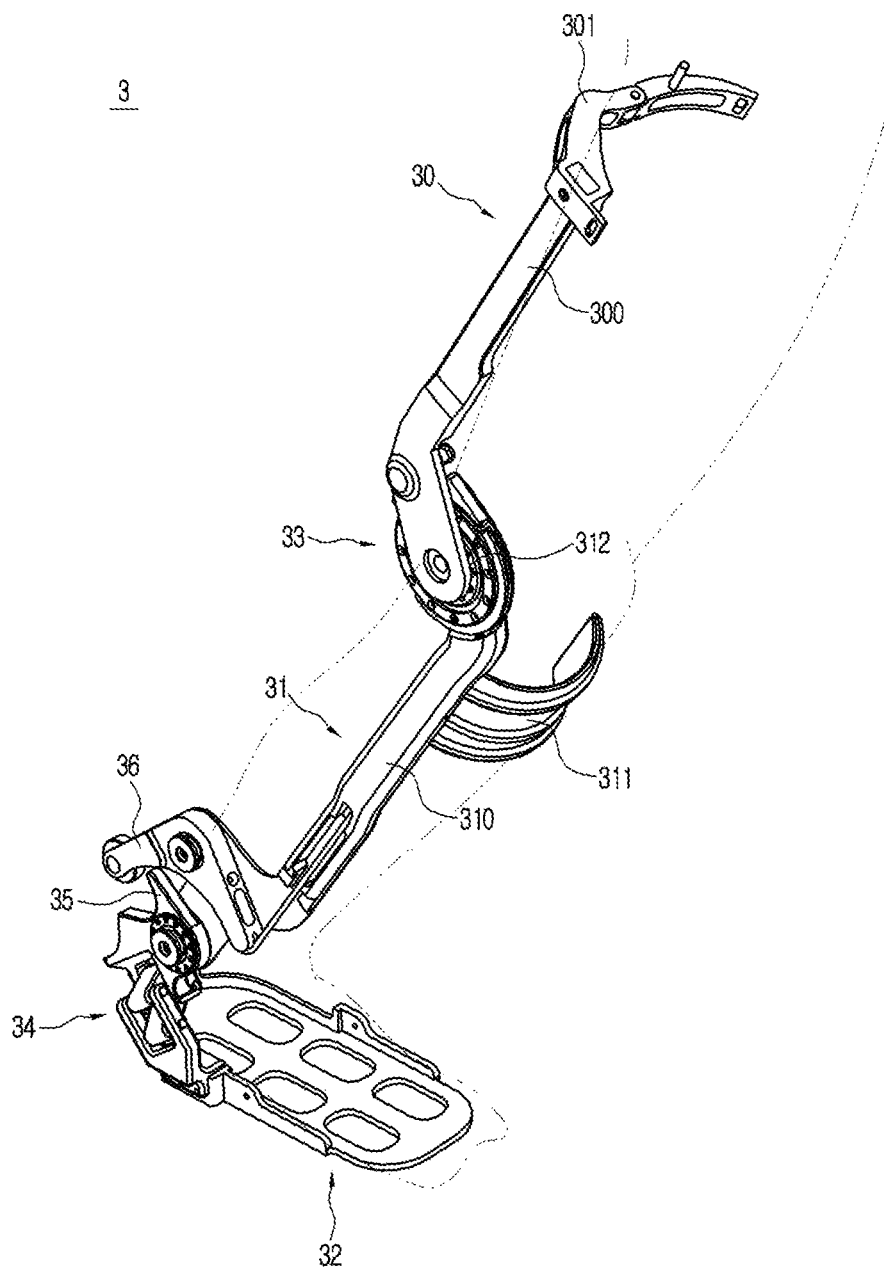
FIG. 9 is a view of a leg supporting apparatus according to another example embodiment.

FIG. 9 is a view of a leg supporting apparatus according to another example embodiment.

Referring to FIG. 9, a leg supporting apparatus 3 according to another example embodiment may include a first frame 30, a second frame 31 connected to the first frame 30 so as to be pivotable around the first joint 33, and a third frame 32 connected to the second frame 31 so as to be pivotable around the second joint 34. The first frame 30 may include a first extension frame 300 extending in a direction in which the user's thigh extends, and a supporting portion 301 may be disposed on the first extension frame 300 and may support the user's hip or thigh. The second frame 31 may be connected to the first frame 30 so as to be pivotable around the first joint 33. The second frame 31 may include a second extension frame 310 extending in a direction in which the user's calf extends. A supporting portion 311 may be disposed on the second extension frame 310 and may support the user's weight transferred via the user's calf.

Figure 10:
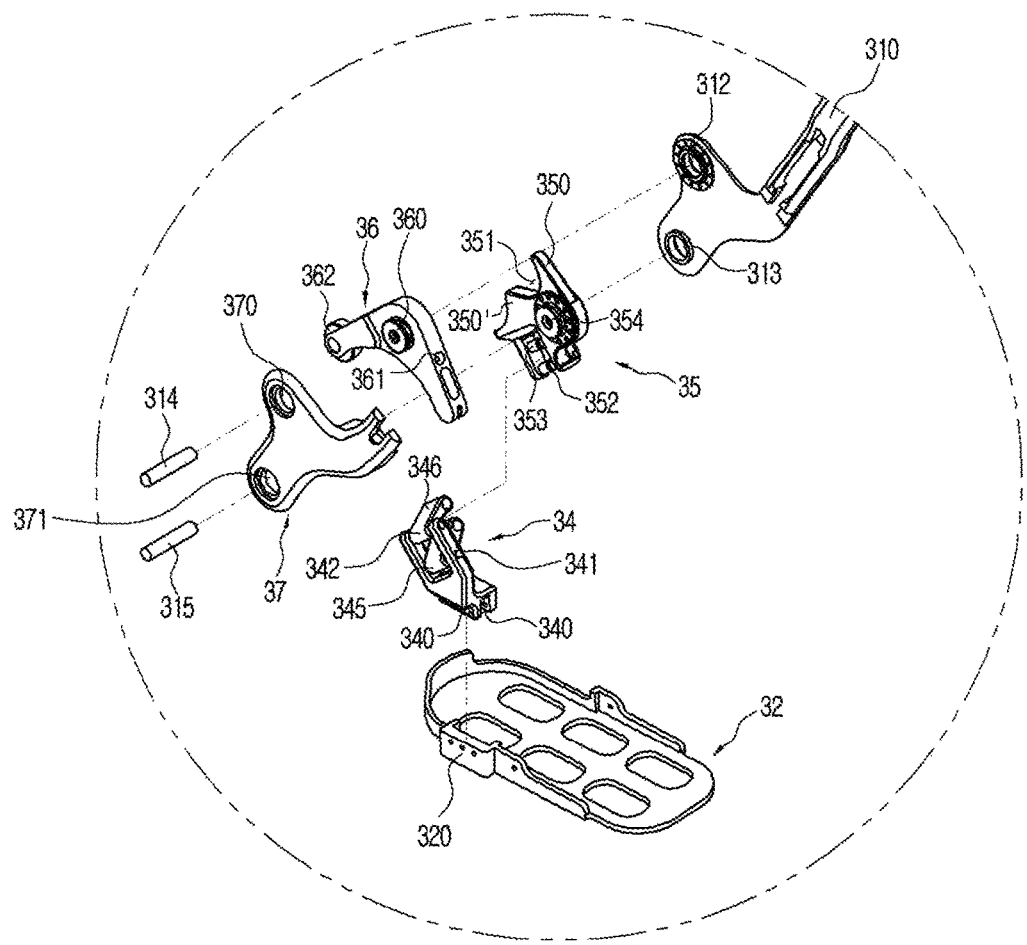
FIG. 10 is a view of an ankle joint portion of the leg supporting apparatus according to another example embodiment.

FIG. 10 is a view of an ankle joint portion of the leg supporting apparatus 3 according to another example embodiment.

Referring to FIG. 10, a third frame 32 may be mounted on the user's foot. The third frame 32 may be pivoted around the second joint 34. For example, the second frame 31 and the third frame 32 may be pivotally connected to each other using a four-bar linkage.

The weight applied to the second frame 31 may be supported by pins 341, 342, 352, and 353 disposed in the four-bar linkage. The four-bar linkage may be connected to the third frame 32 and a cam 35 that will be described later. The pins 352 and 353 may be disposed in the cam 35 in a vertical direction, and the pins 341 and 342 may be disposed in the four-bar linkage in the vertical direction. The lower pin 352 disposed in the cam 35 and the lower pin 341 disposed in the four-bar linkage may be connected to each other using one rotation member 345. Similarly, the upper pin 353 disposed in the cam 35 and the upper pin 342 disposed in the four-bar linkage may be connected to each other using one rotation member 346.

A link coupling portion 320 may be disposed in the third frame 32. A coupling groove 340 into which the link coupling portion 320 may be inserted, may be disposed in a lower portion of the four-bar linkage. The link coupling portion 320 may be inserted into the coupling groove 340, and the four-bar linkage may be coupled to the third frame 32 using a coupling member that passes through the third frame 32 and the four-bar linkage.

The leg supporting apparatus 3 may further include a mounting bracket 37 mounted on the second frame 31. A first hole 370 and a second hole 371 may be formed in the mounting bracket 37. A first hole 312 and a second hole 313 may be formed in a lower side of the second extension frame 310. The first hole 370 and the second hole 371 formed in the mounting bracket 37 may correspond to the first hole 312 and the second hole 313 formed in the lower side of the second extension frame 310. The mounting bracket 37 may be connected to the second extension frame 310 using a first shaft 314 that passes through the first hole 370 of the mounting bracket 37 and the first hole 312 of the second extension frame 310 and a second shaft 315 that passes through the second hole 371 of the mounting bracket 37 and the second hole 313 of the second extension frame 310.

The cam 35 and the latch 36 may be disposed between the mounting bracket 37 and the second extension frame 310. A hole 354 may be formed in the cam 35. The second shaft 315 may pass through the hole 354 formed in the cam 35. A hole 360 may be formed in the latch 36. The first shaft 314 may pass through the hole 360 formed in the latch 36. The latch 36 may be disposed to be rotatable around the first shaft 314. Thus, the cam 35 and the latch 36 may be mounted between the mounting bracket 37 and the second extension frame 310.

Figure 11:
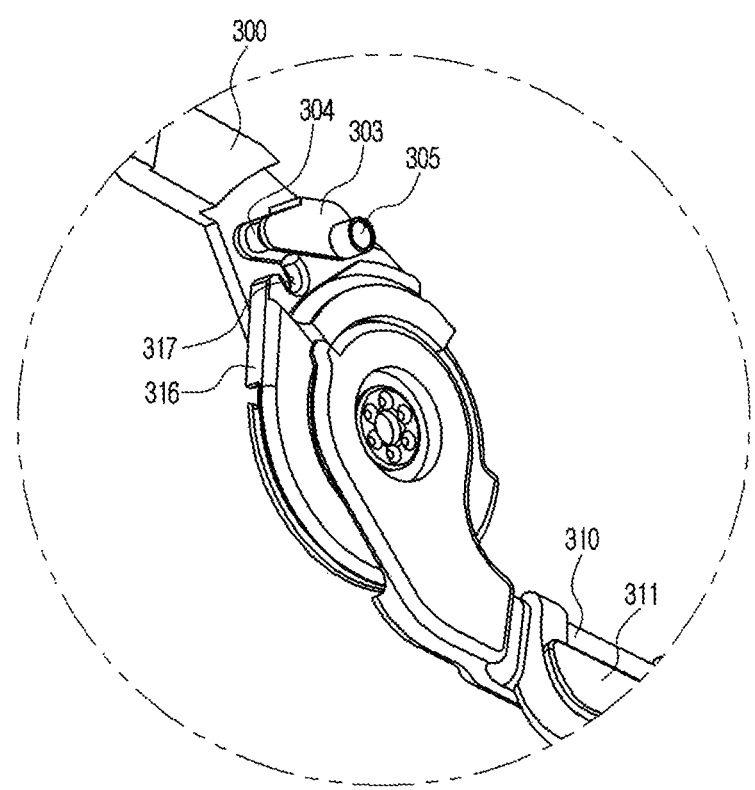
FIGS. 11 and 12 are views of a knee joint portion of the leg supporting apparatus according to another example embodiment.
Figure 12:
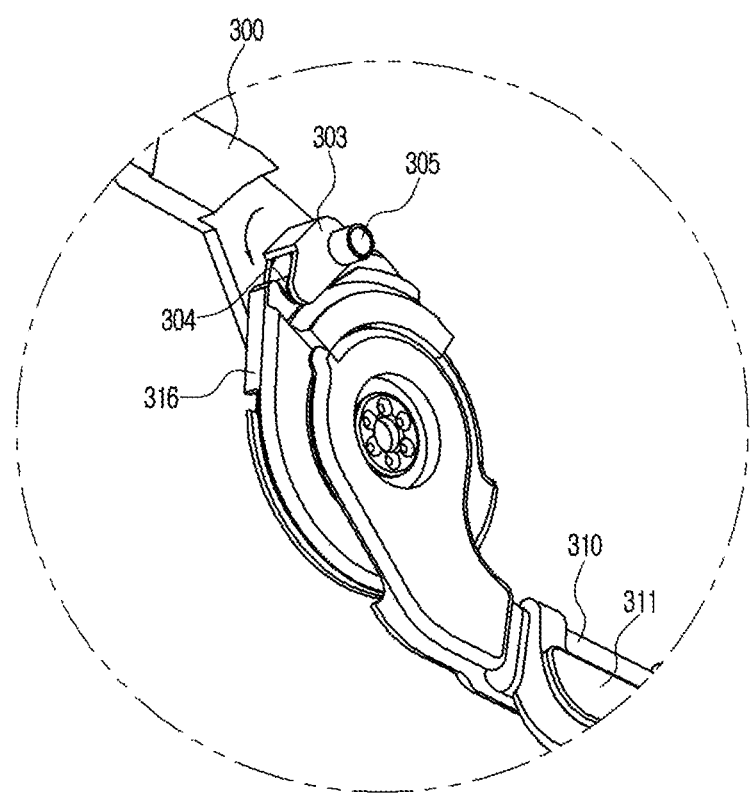

FIGS. 11 and 12 are views of a knee joint portion of the leg supporting apparatus 3 according to another example embodiment.

Referring to FIGS. 11 and 12, a clutch 316 may be disposed on the first joint 33. In a walking mode in which the user walks while wearing the leg supporting apparatus 3, the clutch 316 may cause the first frame 30 and the second frame 31 to be freely pivotable around the first joint 33. In this case, the clutch 316 may be in an unlocked state. When the clutch 316 is in the unlocked state, the first frame 30 may not operate via the cable W.

In order to use the leg supporting apparatus 3 in a supporting mode in which the user's weight is supported, the user may set the clutch 316 in a locked state. When the clutch 316 is in the locked state, the first frame 30 may operate via the cable W, as will be described below.

The clutch 316 may be locked or unlocked by a switch 303. The switch 303 may be disposed on the first frame 30 that is adjacent to the clutch 316. A groove 317 may be formed in the clutch 316. A locking portion 304 may be disposed on the switch 303 and may be inserted into the groove 317. When the locking portion 304 is inserted into the groove 317, the clutch 316 may be locked, and when the locking portion 304 escapes from the groove 317, the clutch 316 may be unlocked. A handle 305 may be disposed on the switch 303, and the user may manipulate the switch 303 by grasping the handle 305 and may lock or unlock the clutch 316. The switch 303 may be automatically locked or unlocked by a motor.

The cam 35 may be disposed on the third frame 32, and the latch 36 may be disposed on the second frame 31. One side of the latch 36 may be provided to slide along an outer surface of the cam 35. The shape of the cam 35 may be similar to or the same as the cam 25 illustrated in FIG. 6. In detail, protrusions 350 and 350' and a concave latch supporting portion 351 may be formed on the cam 35. The protrusions 350 and 350' may include a first protrusion 350 disposed on one side of the latch supporting portion 351 and a second protrusion 350' disposed on the other side of the latch supporting portion 351. The latch 36 includes a roller 362 configured to slide along the latch supporting portion 351 that is the outer surface of the cam 35. A fixing hole 360 may be formed in the latch 36, and the latch 36 may be rotatably be mounted on the second frame 31 by the fixing hole 360 and the shaft 314 that passes through the second frame 31. A cable coupling portion 361 on which the cable W may be mounted, may be disposed on the latch 36.

Figure 13A:
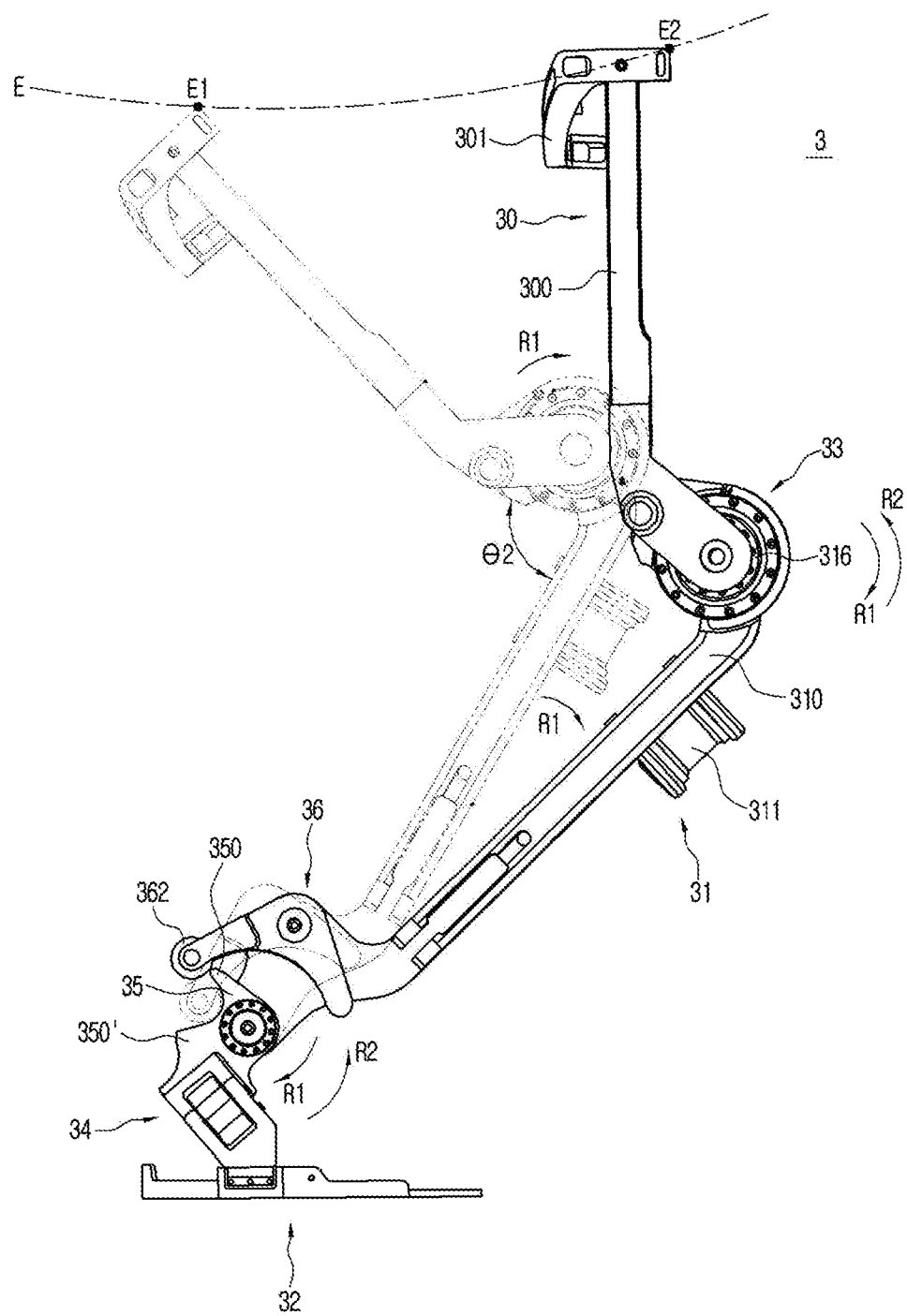
FIGS. 13A and 13B are views of the leg supporting apparatus in operation according to another example embodiment.
Figure 13B:
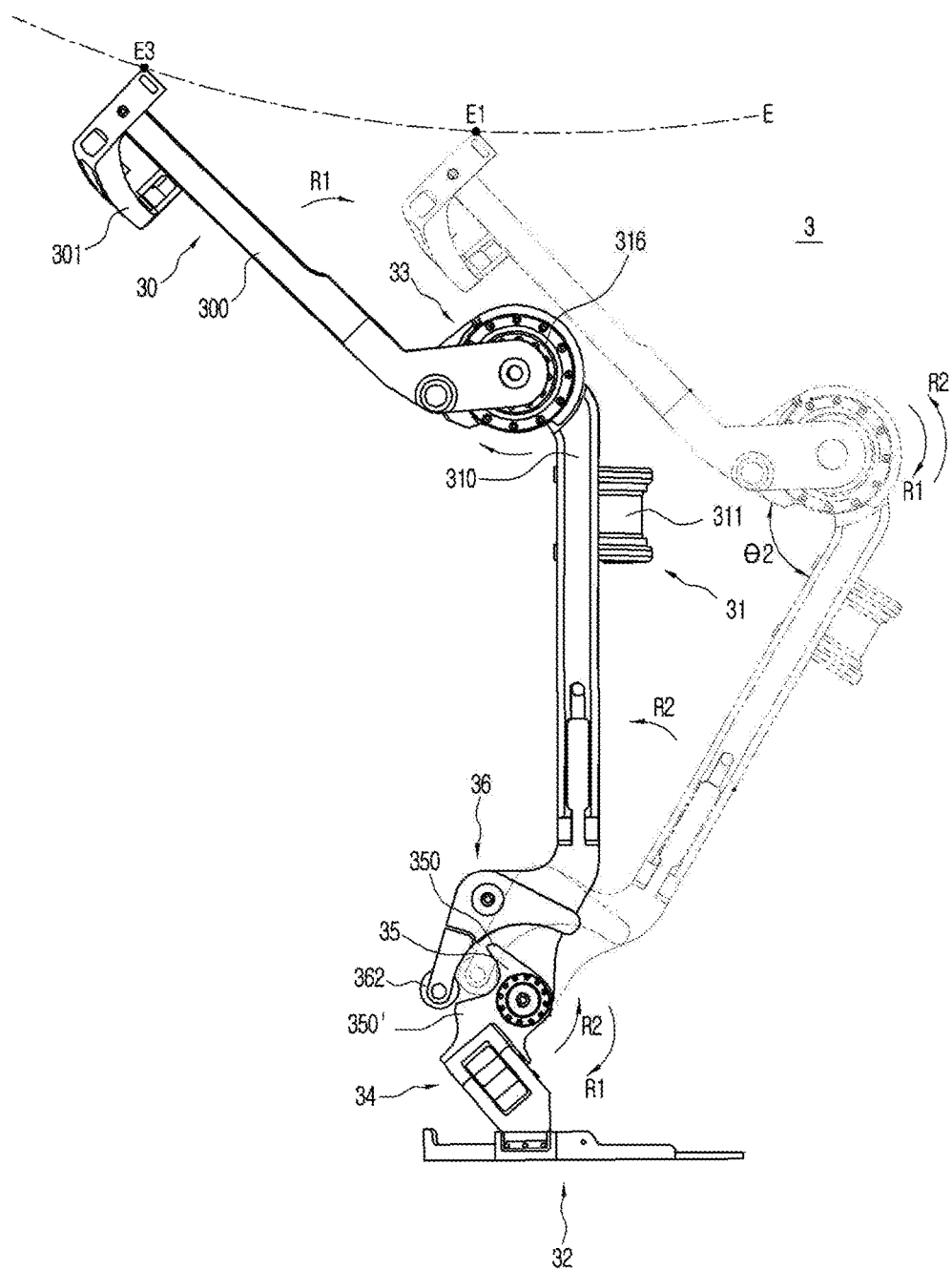

FIGS. 13A and 13B are views of the leg supporting apparatus 3 in operation according to another example embodiment.

Referring to FIGS. 13A and 13B, when the user's weight is supported by the leg supporting apparatus 3, the roller 362 may be supported by the latch supporting portion 351 disposed on the cam 35. When the second frame 31 is pivoted around the second joint 34 in the direction R1 or in the other direction R2 by an external force applied to the second frame 31, the roller 362 may slide along the latch supporting portion 351 of the cam 35 toward the first protrusion 350 or the second protrusion 350'.

As illustrated in FIG. 13A, when the user's weight is supported by the leg supporting apparatus 3 in a state in which the top end of the first frame 30 is placed at the lowest point E1, if the clutch 316 is in a locked state, the second frame 31 may be pivoted around the second joint 34 in the direction R1 by the external force applied to the second frame 31. When the second frame 31 is pivoted around the second joint 34 in the direction R1, the roller 362 of the latch 36 may slide along the latch supporting portion 351 of the cam 35 toward the first protrusion 350, and the cable W may pull the first frame 30. When the first frame 30 is pulled by the cable W, the first frame 30 may be rotated around the first joint 33 in the direction R1, and the top end of the first frame 30 may move to a point E2 along a downwardly-concave curve E.

As illustrated in FIG. 13B, even when the second frame 31 is pivoted around the second joint 34 in the other direction R2 in a state in which the top end of the first frame 30 is placed at the lowest point E1, the first frame 30 may be rotated in the direction R1. When the second frame 31 is pivoted around the second joint 34 in the other direction R2, the roller 362 of the latch 36 may slide along the latch supporting portion 351 of the cam 35 toward the second protrusion 350'. When the roller 362 slides toward the second protrusion 350' of the cam 35, the cable W pulls the first frame 30, and the first frame 30 is rotated around the first joint 33 in the direction R1 so that the top end of the first frame 30 may move to a point E3 along the downwardly-concave curve E.

In a state in which the user's weight is supported and no external force is applied to the first frame 30, the top end of the first frame 30 may be placed at the lowest point E1 of the downwardly-concave curve E. Even when the second frame 31 is rotated around the second joint by an external force applied to the second frame 31 and the top end of the first frame 30 is placed at the point E2 or E3 that is not the lowest point E1 of the downwardly-concave curve E, if the external force applied to the second frame 31 is removed, the top end of the first frame 30 may move to the lowest point E1 of the downwardly-concave curve E again.

In this way, the center of weight of the leg supporting apparatus 3 to which the user's weight is applied, moves along the downwardly-concave curve E so that, even when an external force is applied to the leg supporting apparatus 3, the center of weight of the leg supporting apparatus 3 can be always converged on the lowest point E1 and thus the user's weight can be stably supported.

In the leg supporting apparatus according to the one or other example embodiments, a latch and a first frame are connected to each other using a cable. However, a structure in which a plurality of links is connected, may be used instead of the cable. A unit for transferring force so as to pivot the first frame according to pivoting of the second frame may be referred to as a rotational force transferring member, in addition to the cable or the plurality of links. When the first frame is mounted on the user's thigh, it may be referred to as a thigh frame, when the second frame is mounted on the user' calf, it may be referred to as a calf frame, and when the third frame is mounted on the user's foot, it may be referred to as a foot member.

According to the leg supporting apparatus described above, the center of weight of the leg supporting apparatus moves along a downwardly-concave curve and thus may always be placed at the lowest point. When the user's weight is supported by the leg supporting apparatus, the center of weight of the leg supporting apparatus may be placed at the lowest point. In this state, even when the frame of the leg supporting apparatus is pivoted by a change in the user's posture or an external force applied to the frame, the center of weight of the leg supporting apparatus is not moved downward but moves upward. The center of weight of the leg supporting apparatus that moves upward is returned to the lowest point when the external force is removed, so that the user's weight can be stably supported by the leg supporting apparatus. When a motor is mounted on the first joint of the leg supporting apparatus, the leg supporting apparatus may assist with the user's walking. According to at least one example embodiment, the motor may be controlled via a processor. The processor may be an arithmetic logic unit, a digital signal processor, a microcomputer, a field programmable array, a programmable logic unit, a microprocessor or any other device capable of responding to and executing instructions in a defined manner such that the processor is programmed with instructions. The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion.

The example embodiment in which the end of the first frame included in the leg supporting apparatus moves along the downwardly-concave curve, has been described. However, the leg supporting apparatus may be configured in such a way that the end of the first frame moves along, for example, a straight line that is parallel to the bottom surface, or along another direction. The leg supporting apparatus may be configured in such a way that the shape of the cam is changed so that the end of the first frame may move along the downwardly-concave curve, a straight line that is horizontal with respect to the bottom surface, or a line extending in another direction.

As described above, in a link assembly and a leg supporting apparatus using the same according to the one or more example embodiments, a user's weight can be stably supported.

Although a few example embodiments have been shown and described, it would be appreciated by those skilled in the art that changes may be made in these example embodiments without departing from the principles and scope defined in the claims and their equivalents.

What is claimed is:

1. A leg supporting apparatus comprising:
    a calf frame configured to be mounted on a user's calf;
    a thigh frame configured to be mounted on the user's thigh and pivotally connected to the calf frame via a first joint;
    a clutch at the first joint and configured to be in a locked state or in an unlocked state, where in the locked state the calf frame is not pivotable with respect to the thigh frame; and
    a rotational force transferring member configured to transfer a rotational force to the thigh frame;
    wherein an end of the rotational force transferring member is fixed to a side of the first joint facing a walking direction of the leg supporting apparatus and is connected to the thigh frame.

2. The leg supporting apparatus of claim 1, wherein a point at which the thigh frame is pivoted in one direction, regardless of a direction in which the calf frame is pivoted, is included in a downwardly-concave curve along which an end of the thigh frame moves.

3. The leg supporting apparatus of claim 2, wherein the point at which the thigh frame is pivoted in one direction, regardless of the direction in which the calf frame is pivoted, is a lowest point of the downwardly-concave curve.

4. The leg supporting apparatus of claim 1, wherein the rotational force transferring member comprises at least one of a cable and one or more links.

5. The leg supporting apparatus of claim 1, wherein a rotational force of the rotational force transferring member is transferred to the thigh frame when the clutch is in the locked state.

6. The leg supporting apparatus of claim 1, further comprising:
    a foot member pivotally connected to the calf frame.

7. The leg supporting apparatus of claim 6, further comprising:
    a cam at a second joint to which the calf frame and the foot member are connected, the cam having a first protrusion and a second protrusion.

8. The leg supporting apparatus of claim 7, wherein the first protrusion and the second protrusion are asymmetrically formed.

9. The leg supporting apparatus of claim 7, further comprising:
    a latch on the calf frame, the latch having one side configured to slide along an outer surface of the cam.

10. The leg supporting apparatus of claim 9, further comprising:
    a concave latch supporting portion between the first protrusion and the second protrusion of the cam, and the latch is configured to slide along the latch supporting portion.

11. The leg supporting apparatus of claim 9, wherein the latch comprises a roller configured to slide along the outer surface of the cam.

12. The leg supporting apparatus of claim 9,
    wherein one side of the rotational force transferring member is fixed to the latch.

13. The leg supporting apparatus of claim 12, further comprising:
    a guide groove in the latch, the guide groove being configured to guide the rotational force transferring member.

14. The leg supporting apparatus of claim 1, wherein, when an end of the thigh frame is placed at a lowest point of a downwardly-concave curve, an angle between the calf frame and the thigh frame is between about 60° and about 135°.

15. The leg supporting apparatus of claim 14, the angle between the calf frame and the thigh frame is between about 60° and about 135° when the clutch is in the locked state.

16. The leg supporting apparatus of claim 1, wherein an angle between the thigh frame and a bottom surface is between about −20° and about 90°.

17. The leg supporting apparatus of claim 1, wherein an angle between the calf frame and a bottom surface is between about 30° and about 90°.

18. The leg supporting apparatus of claim 1, wherein a path of a center of gravity of the leg supporting apparatus intersects a downwardly-concave curve at a lowest point thereof.

19. A link assembly comprising:
a calf frame configured to be mounted on a user's calf;
a thigh frame configured to be mounted on the user's thigh and connected to the calf frame via a joint;
a clutch at the joint, the clutch being configured to be in a locked state or in an unlocked state, where in the locked state the calf frame is not pivotable with respect to the thigh frame and the user's weight is supported with the calf frame; and
a rotational force transferring member configured to transfer a rotational force to the thigh frame;
wherein the thigh frame is configured to operate in one of a walking mode in the unlocked state, in which the thigh frame is freely pivotable with respect to the calf frame, and in a supporting mode, in which the clutch is in a locked state; and
wherein an end of the rotational force transferring member is fixed to a side of the joint facing a walking direction of the link assembly and is connected to the thigh frame.

20. The link assembly of claim 19, wherein, in the supporting mode, when an external force is applied, an end of the thigh frame moves along a downwardly-concave curve.

21. The link assembly of claim 19, wherein a path of a center of gravity of the link assembly intersects a downwardly-concave curve at a lowest point thereof.

22. The link assembly of claim 19, wherein in the locked state of the clutch, an angle between the calf frame and the thigh frame is between about 60° and 135°.

23. A supporting apparatus comprising:
a first frame configured to be mounted on a first body portion;
a second frame configured to be mounted on a second body portion;
a clutch at a joint to which the first frame and the second frame are connected, the clutch being configured to be in a locked state, where the first frame is not pivotable with respect to the second frame, or in an unlocked state in which the first frame is freely pivotable with respect to the second frame; and
a rotational force transferring member configured to transfer a rotational force to the second frame;
wherein an end of the rotational force transferring member is fixed to a side of the joint facing a walking direction of the supporting apparatus and is connected to the second frame.

24. The supporting apparatus of claim 23, wherein the second body portion is coupled to the first body portion.

25. The supporting apparatus of claim 23, wherein:
in a walking mode, the second frame is freely pivotable with respect to the first frame; and
in a supporting mode, the second frame is not freely pivotable with respect to the first frame and supports a weight of at least the first body portion and the second body portion.

26. The supporting apparatus of claim 23,
wherein a rotational force of the rotational force transferring member is transferred to the second frame when the clutch is in a locked state.

27. The supporting apparatus of claim 23, wherein a path of a center of gravity of the supporting apparatus intersects a downwardly-concave curve at a lowest point thereof.

28. The supporting apparatus of claim 23, wherein in the locked state of the clutch, an angle between the first frame and the second frame is between about 60° and 135°.

* * * * *